Dec. 23, 1975 D. J. S. BAILEY Plant Pat. 3,818
ROSE PLANT
Filed May 10, 1973
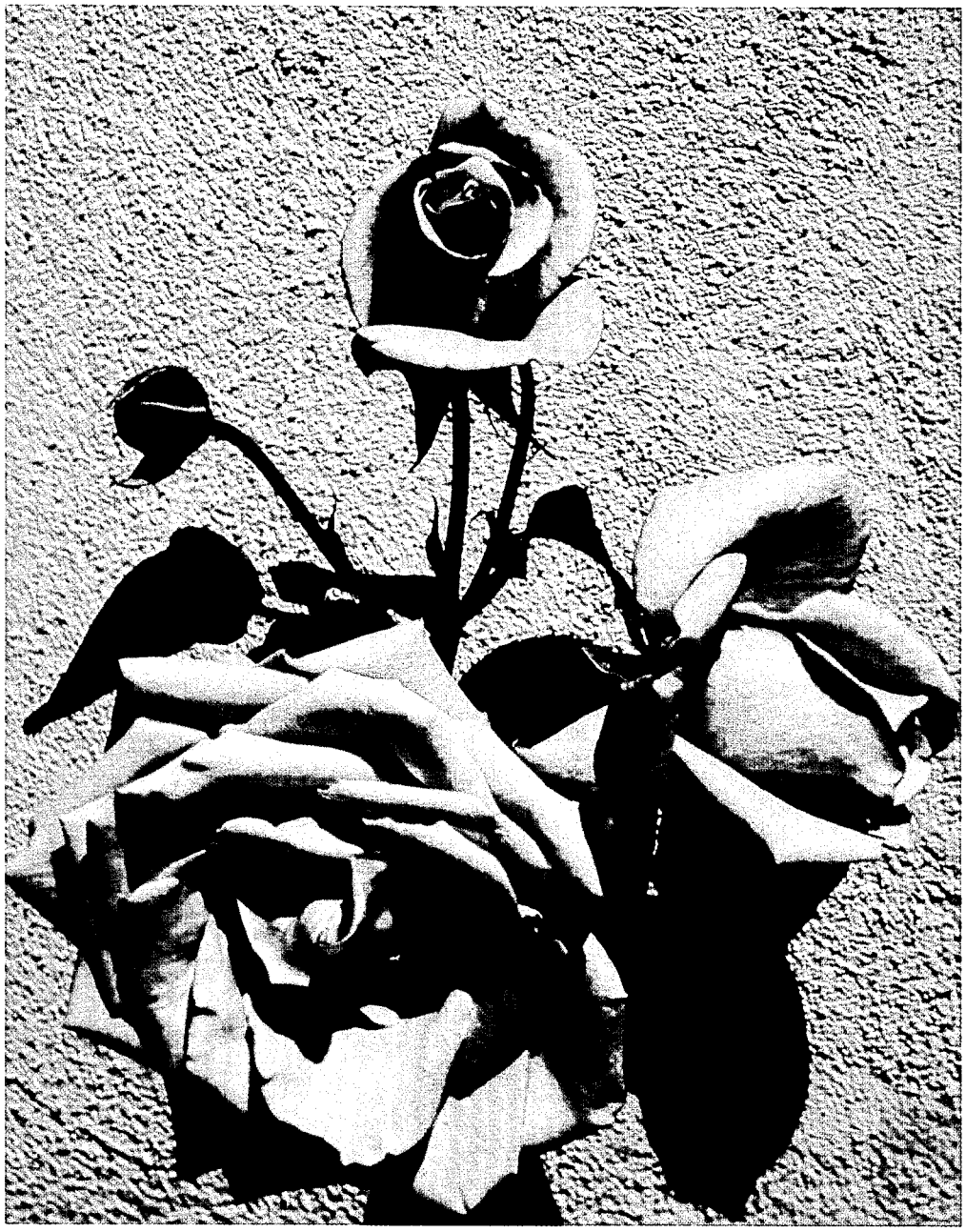

United States Patent

Plant Pat. 3,818

Patented Dec. 23, 1975

3,818

ROSE PLANT

Dorothy Jean Searles Bailey, Bakersfield, Calif., assignor to San Joaquin Rose Co., McFarland, Calif.

Filed May 10, 1973, Ser. No. 359,094

Int. Cl. A01h 5/00

U.S. Cl. Plt.—18 1 Claim

The present invention relates to a new and distinct variety of rose plant of the hybrid tea class, which was originated by me by crossing the rose variety known as "Simone" (Plant Pat. No. 1,847) with the variety known as "Sterling Silver" (Plant Pat. No .1,433).

As the result of this breeding, I have produced a new and improved rose variety which is distinguished from its parents, as well as from all other rose varieties of which I am aware, as evidenced by the following unique combination of characteristics which are outstanding therein:

(1) A moderately tall, well shaped bush having upright and well-branched canes;
(2) Abundant, medium large, dark green foliage;
(3) Continuous abundant bloom throughout the growing season, with flowers borne mostly singly on strong long and medium long stems;
(4) Pointed buds of approximately 1¼ inches in length, opening into a large high-centered bloom, of regular petal conformation, very double with 50 to 55 petals, and when fully opened, from 4 to 5 inches across the whole bloom;
(5) A distinctive color range chiefly in the Red Purple series (RHS); and
(6) A strong Centifolia fragrance.

In comparison with its parent varieties, the new variety has inherited the vigorous bush and improved mildew resistance from the parent "Simone." The refined high-centered bloom and strong Centifolia fragrance are inherited from the parent "Sterling Silver." The weak necks usually exhibited in "Simone" have been corrected in this new variety, by the inheritance of the stiff necks supporting the blooms of "Sterling Silver." The new variety is an improvement over both the parent varieties due to the inheritance of the best characteristics of each, and easily distinguishable from each parent. This is a distinctive new variety and would not be confused with any new variety I am aware of.

The cross that resulted in this new variety was made in 1963 by me, at Shafter, Calif. It was first asexually reproduced in 1965, in Shafter, by means of budding. The distinguishing characteristics are held through successive propagations.

The accompanying photographs show typical specimens of vegetative growth and flowers of my new variety in different stages of development and are depicted in color as nearly true as it is reasonably possible with color photography.

The following is a detailed description of my new variety, with color terminology in accordance with the Royal Horticultural Society Colour Chart (RHS) where such designations are used. except where general color terms of ordinary dictionary significance are obvious, as based upon observations of specimens grown at Shafter, Calif.:

TYPE: Half-hardy; bush; outdoor; seedling; for cut flowers and garden decoration.
CLASS: Hybrid tea.
BREEDING: Seedling.
Seed parent—"Sterling Silver."
Pollen parent—"Simone."
DATE OF SOWING: 1963.
PROPAGATION: Holds its distinguishing characteristics through succeeding propagations.

FLOWER

CONTINUITY: Continuous.
FRAGRANCE: Strong; centifolia.
FLOWERS BORNE: Usually singly, several to stem; on normal, strong, medium and long stems.
QUANTITY OF BLOOM: Abundant outdoors.
BUD:
Peduncle—Medium long; medium in thickness; erect; yellowish green; almost smooth.
Before calyx breaks. Size—Medium. Form—Pointed oval; with foliaceous appendages on the surface of the bud; slender; foliaceous parts extending beyond the tip of the bud equal to less than ¼ of its length.
As calyx breaks: Color—No significant change.
As first petal opens: Size—Medium. Inside—Rose Purple 5 33/1, Plate 140. Opening—It does open up well. It is not retarded from opening by cold, hot, wet, or dry weather.
BLOOM:
Size—When fully open, 4–5 inches.
Petalage—Very double, from 50 to 55 petals; arranged regularly.
Form—High centered; petals being at first rolled outward; becoming later, at maturity, loosely rolled outward.
PETALS:
Texature.—Thick; with inside velvety; with outside satiny. Shape: Outside—ovate, with 1 offcenter notch. Intermediate—ovate, with 1 notch. Inside—ovate linear; scalloped irregular, with 1 notch. Color: Thickened petal sac, Soft Yellow.

This description of a newly opened flower was made from a rose grown outdoors, September 1971, Shafter, Calif.

Color: In the bud color starts out as near RHS 62B gradually lightening to RHS 62C and 62D as the blossom matures. Three days open—Rose Purple 5 33/3.
Behavior—Drops off cleanly.
Flower longevity—Bush in garden 5 days in October. Cut roses grown outdoors, kept at living room temperatures 3 days in October.

REPRODUCTIVE ORGANS

STAMENS: Many; arranged regularly about pistils; mixed with a few petaloids.
Color—Light Yellow.
FILAMENTS: Medium long; yellow; most with anthers.
ANTHERS: Medium; yellow; open at various times.
POLLEN: Sparse; lemon.
PISTILS: Many.
STYLES: Uneven; short and medium long; bunched.
STIGMA: Light yellow.
OVARIES: All enclosed in calyx.
HIPS: None observed.
SEPALS: Permanent; broad, straight.
Color—Light Grey.
SEEDS: None observed.

PLANT

FOLIAGE: Leaves, compound of 5; abundant; medium large; moderately heavy.
Leaflets—Ovoid, mucronate apex; base round; margin doubly serrate. Color: Mature—Upper surface—Dark Green. Under surface—Grey-Green. Young—Upper surface—Green-Bronze. Under surface—Bronze-Red.
Rachis (the supporting stem of the compound leaf), medium heavy. Upper side—Smooth. Under side—Moderately prickly.

Stipules—Moderately short; wide; with short, blunt points, turning out at an angle of less than 45°.

Disease and insect resistance—Good average resistance to mildew and rust as determined by comparison with other varieties in the field at Shafter over several years.

GROWTH:

Habit—bushy, upright, many branches.

Growth—Moderately vigorous.

Canes—Medium.

Main stems—Bright green. Thorns—Few; medium in length; straight; with long, narrow base. Prickles—None. Hairs—None.

Branches—Green. Thorns—Few; medium in length; straight and hooked downward; with long, narrow base. Prickles—None. Hairs—None.

New Shoots—Green-Bronze. Thorns—Few; medium in length; straight; with long, narrow base. Red with yellow points. Prickles—Few; reddish. Hairs—None.

I claim:

1. A new and distinct variety of rose plant of the hybrid tea class, substantially as herein shown and described, characterized particularly as to novelty by the unique combination of a moderately tall, well-shaped bush having upright and well-branched canes; abundant, medium large, dark green foliage; continuous abundant bloom throughout the growing season, with flowers borne mostly singly on strong, long and medium stems; pointed buds of approximately 1¼ inches in length, opening into a large high-centered bloom of regular petal conformation, very double with 50 to 55 petals, and when fully opened, from 4 to 5 inches across the whole bloom; a distinctive color range chiefly in the range of RHS 62B gradually lightening to RHS 62C and 62D and a strong Centifolia fragrance.

References Cited

UNITED STATES PATENTS

P.P. 999 12/1950 Fisher ---------- Plants—11

ROBERT E. BAGWILL, Primary Examiner